United States Patent
Wei

(10) Patent No.: US 9,859,570 B2
(45) Date of Patent: Jan. 2, 2018

(54) ELECTRONIC APPARATUS AND ASSOCIATED METHODS

(71) Applicant: Nokia Technologies Oy, Espoo (FI)

(72) Inventor: Di Wei, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 51 days.

(21) Appl. No.: 15/037,305

(22) PCT Filed: Nov. 6, 2014

(86) PCT No.: PCT/FI2014/050835
§ 371 (c)(1),
(2) Date: May 17, 2016

(87) PCT Pub. No.: WO2015/086888
PCT Pub. Date: Jun. 18, 2015

(65) Prior Publication Data
US 2016/0293973 A1    Oct. 6, 2016

(30) Foreign Application Priority Data
Dec. 12, 2013    (GB) .................................. 1322029.8

(51) Int. Cl.
*H01M 10/052*    (2010.01)
*H01M 10/0525*    (2010.01)
(Continued)

(52) U.S. Cl.
CPC ............ *H01M 6/32* (2013.01); *G01N 27/308* (2013.01); *G01N 27/333* (2013.01);
(Continued)

(58) Field of Classification Search
CPC ..................... H01M 10/052; H01M 10/0525
See application file for complete search history.

(56) References Cited

U.S. PATENT DOCUMENTS

| 4,894,301 A | 1/1990 | Dyer |
| 5,731,105 A | 3/1998 | Fleischer et al. |

(Continued)

FOREIGN PATENT DOCUMENTS

| EP | 1294039 | 3/2003 |
| GB | 2145282 | 3/1985 |

(Continued)

OTHER PUBLICATIONS

International Search Report and Written Opinion received for corresponding Patent Cooperation Treaty Application No. PCT/FI2014/050835, dated Mar. 9, 2015, 1 pages.

(Continued)

*Primary Examiner* — Olatunji Godo
(74) *Attorney, Agent, or Firm* — Nokia Technologies Oy

(57) ABSTRACT

An apparatus comprising an insulating substrate (101); at least two charge collectors (102, 103) spaced apart on the substrate (101) surface; a proton-generating electrode layer (104) configured to generate proton charge carriers; a proton-accepting electrode layer (105) configured to accept the generated proton charge carriers, wherein each of the proton-generating electrode layer (104) and proton-accepting electrode layer (105) are configured to be electrically connected to a different one of the respective charge collectors (102, 103), and to overlap in a junction region such that the charge carriers of the layers can be transferred between the proton-generating (104) and proton-accepting (105) electrode layers to thereby generate a voltage.

19 Claims, 4 Drawing Sheets

(51) Int. Cl.
  *H01M 6/32* (2006.01)
  *G01N 27/414* (2006.01)
  *H01M 4/04* (2006.01)
  *H01M 6/40* (2006.01)
  *G01N 27/30* (2006.01)
  *G01N 27/333* (2006.01)

(52) U.S. Cl.
  CPC ...... *G01N 27/4141* (2013.01); *H01M 4/0402* (2013.01); *H01M 6/40* (2013.01); *H01M 2220/30* (2013.01)

(56) References Cited

U.S. PATENT DOCUMENTS

| | | | |
|---|---|---|---|
| 2006/0057455 A1 | 3/2006 | Guntow et al. | |
| 2011/0097625 A1 | 4/2011 | Bedjaoui et al. | |
| 2013/0043475 A1 | 2/2013 | Kim et al. | |
| 2013/0164619 A1* | 6/2013 | Yamakaji | H01M 4/134 429/217 |
| 2013/0266859 A1* | 10/2013 | Todoriki | H01M 4/625 429/211 |
| 2013/0309571 A1* | 11/2013 | Yoon | H01M 4/583 429/213 |
| 2013/0313522 A1 | 11/2013 | Nourbakhsh et al. | |
| 2013/0313523 A1 | 11/2013 | Yun et al. | |
| 2013/0314844 A1* | 11/2013 | Chen | C01B 31/043 361/502 |

FOREIGN PATENT DOCUMENTS

| | | |
|---|---|---|
| GB | 2449926 | 10/2008 |
| WO | 0141232 | 6/2001 |

OTHER PUBLICATIONS

Search Report received for corresponding GB Patent Application No. 1322029.8, dated Jun. 12, 2014 (4 pages).

Thin Solid Films, vol. 534, 2013, Sarfraz et al, "Printed hydrogen 17-19 sulfide gas sensor on paper substrate based on polyaniline composite", pp. 621-628.

Tanaka et al., "Application of screen-printed 17-19 catalytic electrodes to MEMS-based fuel cells", Transactions of the Institute of Electrical Engineers of Japan, Part E, 9-12, 14, vol. 125-E, 2005, pp. 413-417.

* cited by examiner

ELECTRONIC APPARATUS AND ASSOCIATED METHODS

RELATED APPLICATION

This application was originally filed as PCT Application No. PCT/FI2014/050835 filed Nov. 6, 2014, which claims priority benefit from GB Patent Application No. 1322029.8, filed Dec. 12, 2013.

TECHNICAL FIELD

The present disclosure relates to the field of electronics, associated methods and apparatus. Certain disclosed example aspects/embodiments relate to portable electronic devices, in particular, so-called hand-portable electronic devices which may be hand-held in use (although they may be placed in a cradle in use). Such hand-portable electronic devices include so-called Personal Digital Assistants (PDAs), tablet PCs, smart watches and other wearable electronics.

The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), down-loading/sending of data functions, image capture function (e.g. using a (e.g. in-built) digital camera), and gaming functions.

BACKGROUND

Electronic devices are becoming more and more ubiquitous, with users interacting with electronics in many different ways. For example, people carry portable electronic devices with them in the form of smartphones, tablet computers, laptops, smart-watches, e-book readers and various wearable electronics.

One or more aspects/embodiments of the present disclosure may or may not address one or more of these issues.

The listing or discussion of a prior-published document or any background in this specification should not necessarily be taken as an acknowledgement that the document or background is part of the state of the art or is common general knowledge.

SUMMARY

According to a first embodiment, there is provided an apparatus, the apparatus comprising:
an insulating substrate;
at least two charge collectors spaced apart on the substrate surface;
a proton-generating electrode layer configured to generate proton charge carriers;
a proton-accepting electrode layer configured to accept the generated proton charge carriers,
wherein each of the proton-generating electrode layer and proton-accepting electrode layer are configured to be electrically connected to a different one of the respective charge collector, and to overlap in a junction region such that the charge carriers of the layers can be transferred between the proton-generating and proton-accepting electrode layers to thereby generate a voltage.

The proton-generating electrode layer may comprise graphene oxide. The proton-accepting electrode layer may comprise at least one of reduced graphene oxide and conjugated polymer ink. Reduced graphene oxide may be generated by treating graphene oxide with an aqueous solution of alkali, such as KOH (potassium hydroxide), or ascorbic acid. When making reduced graphene oxide for the proton-accepting electrode layer it has been found that, when using KOH, mixing graphene oxide with an aqueous solution of 3.5 M KOH to make the final mixture solution with a pH of 13 gives the greatest battery cell voltage whilst allowing a stable ink to be formed. That is, a lower pH (reduced GO from ascorbic acid pH<3) may give a reduced cell voltage whereas a higher pH (e.g. pH 14) may cause precipitates to be formed in the ink.

At least one of the charge collectors may be directly in contact with the substrate. At least one of the charge collectors may be supported by the substrate but not directly in contact with the substrate.

At least one of the electrode layers may comprise one or more of a plurality of fully or partially oxidised graphene flakes. The plurality of fully or partially oxidised graphene flakes may have various functional groups attached thereto. Furthermore, the size and number of the oxidised graphene layers may vary. Graphene oxide solution (concentration: 1 g/L; composition: carbon (79%), oxygen (20%); flake size: 0.5-0.7 µm; and thickness: 1 atomic layer (at least 60%)) can be obtained from Graphene Square Inc. and deposited using spray coating, drop casting, spin coating or inkjet printing.

Protons charge carriers may be generated by charge-releasing functional groups, the charge-releasing functional groups comprising one or more of a carboxyl, hydroxyl and epoxy group.

The substrate may be at least one of: a flexible substrate (e.g. a substrate which can be bent or otherwise deformed such as polythene); a resilient substrate (e.g. rubber); and a foldable substrate (e.g. a substrate which retains a crease when folded, such as paper). The substrate may comprise at least one of: a polymer sheet, and glass. The substrate may comprise paper.

At least one of the charge collectors may comprise silver or copper (in the form of conductive inks, for example). The charge collectors may be configured to be more conductive than the electrode layers.

At least one of the charge collectors and the electrode layers may be printed onto the substrate. At least one of the charge collectors and the electrodes may be formed from ink. At least one of the charge collectors and the electrode layers may be drawn or painted onto the substrate (e.g. using pens or brushes).

The apparatus may comprise an electrolyte layer, configured to trap water or other electrolyte to encourage protonation of graphene oxide. In battery cell embodiments this electrolyte layer may help maintain a high and constant voltage. The electrolyte layer may comprise Nafion® or polyvinyl alcohol film. The electrolyte may be a room temperature ionic liquid or gel.

The apparatus may comprise a protective layer covering at least the proton-generating layer, the protective layer comprising a fluid-impermeable material.

The apparatus may be one or more of a battery, a FET and a sensor.

For example, embodiments may be used as a Chemical FET or ion selective FET (ISFET), in which a chemical process is used to change the voltage between the source and drain. That is, the junction region can function as the gate in a FET such that the gate voltage varies with different humidity/pH.

The proton-generating layer may be configured to generate proton charge carriers in response to a fluid being present, such that the voltage produced may be used as an indicator of the amount of fluid present.

According to a further embodiment, there is provided a device comprising an array of connected apparatuses, wherein the connected apparatuses are arranged on a common substrate, the connections being configured to allow the apparatuses to act in concert to provide a cumulative effect. The cumulative effect may include providing a larger voltage than would be providing a larger voltage and/or storing more energy than would be available from a single battery cell apparatus.

The apparatus may be one or more of an electronic device, a portable electronic device, a portable telecommunications device, a sensor and a module for any of the aforementioned devices.

According to a further embodiment, there is provided a method, the method comprising:
 providing an insulating substrate;
 providing at least two charge collectors spaced apart on the substrate surface;
 providing a proton-generating electrode layer configured to generate proton charge carriers;
 providing a proton-accepting electrode layer configured to accept the generated proton charge carriers,
 wherein each of the proton-generating electrode layer and proton-accepting electrode layer are configured to be electrically connected to a different one of the respective charge collectors, and to overlap in a junction region such that the charge carriers of the layers can be transferred between the proton-generating and proton-accepting electrode layers to thereby generate a voltage.

At least one of the charge collectors and the electrodes may be provided on the substrate by a printing process.

The steps of any method disclosed herein do not have to be performed in the exact order disclosed, unless explicitly stated or understood by the skilled person.

Corresponding computer programs (which may or may not be recorded on a carrier) for implementing one or more of the methods disclosed herein are also within the present disclosure and encompassed by one or more of the described example embodiments. The computer program may be stored on a non-transient medium such as a CD or DVD.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which.

DESCRIPTION OF SPECIFIC ASPECTS/EMBODIMENTS

Figure 1A:
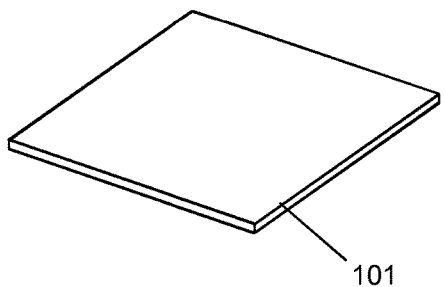
FIGS. 1a-e show a manufacturing process used to create a battery cell.

New types of electronic devices are being developed (e.g. smart-phones, smart-watches e-book readers, tablet computers, flexible mobile phones). This has encouraged the development of different types of electronics to suit. For example, the increased processing power of portable electronic devices has driven research to increase the capacity, and to reduce the weight, of batteries.

The present disclosure relates to an apparatus, the apparatus comprising: an insulating substrate; at least two charge collectors spaced apart on the substrate surface; a proton-generating electrode layer configured to generate proton charge carriers; a proton-accepting electrode layer configured to accept the generated proton charge carriers, wherein each of the proton-generating electrode layer and proton-accepting electrode layer are configured to be electrically connected to a different one of the respective charge collectors, and to overlap in a junction region such that the charge carriers of the layers can be transferred between the proton-generating and proton-accepting electrode layers to thereby generate a voltage.

It will be appreciated that the resulting voltage may be used in a variety of applications. For example, the voltage may be used to power other electronic components (the apparatus in this case acting as a battery or cell). Further, the voltage may be used to indicate the condition and environment of the apparatus (the apparatus in this case acting as a sensor).

FIG. 1a-e shows the manufacture of an embodiment of a battery cell apparatus, the apparatus comprising:
 an insulating substrate 101;
 at least two charge collectors 102, 103 spaced apart on the substrate surface;
 a proton-generating electrode layer 104 configured to generate proton charge carriers;
 a proton-accepting electrode layer 105 configured to accept the generated proton charge carriers,
 wherein each of the proton-generating electrode layer 104 and proton-accepting electrode layer 105 are configured to be electrically connected to a different one of the respective charge collectors 102, 103, and to overlap in a junction region such that the charge carriers of the layers can be transferred between the proton-generating and proton-accepting electrode layers 104, 105 to thereby generate a voltage.

FIG. 1a shows a substrate layer 101, which in this case is paper (cellulose). Using a paper substrate allows the battery cell apparatus to be folded. Using a foldable substrate (such as paper), with appropriate electrically active components (e.g. such as charge collectors and/or electrodes) that can withstand folding, may allow foldable electronics to be produced. Foldable electronics allow an edge (or crease) to be formed in the substrate at the fold, such that an edge (or crease) is retained even after unfolding. Foldable electronics may allow more permanent and stable three dimensional configurations to be adopted than would be available using fully flexible electronics (i.e. electronics which may be deformed but which would not retain a crease).

Also, because paper is porous, a paper substrate may function as a reservoir for the active inks and enable formation of protonation junctions without causing short-circuitry. Other advantages of paper include that it is inexpensive, lightweight, and disposable (environmentally friendly). Paper is also a common medium available which is readily available to the public. This may allow small-scale users to manufacture devices using common equipment. That is, the users may print their own electronics (e.g. batteries) at home.

Figure 1B:
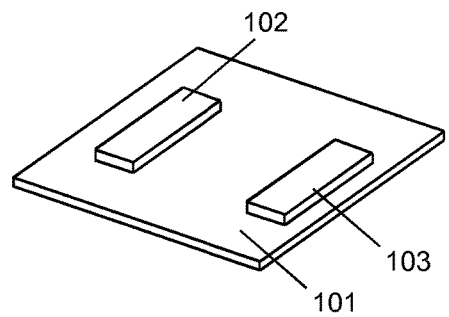

Two charge collectors 102, 103 are then printed onto the same surface (the top surface) of the substrate (as shown in FIG. 1b). Because the substrate 101 is electrically insulating, the substrate 101 does not provide short-circuit between the charge collectors. It will be appreciated that the substrate 101 need only be electrically insulating during periods of operation of the apparatus.

In this case, the charge collectors 102, 103 comprise silver ink printed onto the surface of the substrate 101. It will be appreciated that other conducting material may be used (e.g. copper ink). Silver or copper inks can be printed on paper with designed patterns. The charge collectors are configured to have low resistance. For example, silver and copper may have a sheet resistance of between 0.1-0.5Ω (e.g. 0.4Ω) depending on the thickness of the charge collector layer. In contrast, graphene oxide (which may be used as an electrode material) is an insulator and graphene oxide layers of <50 nm in thickness have sheet resistances of >GΩ/sq.

Figure 1C:
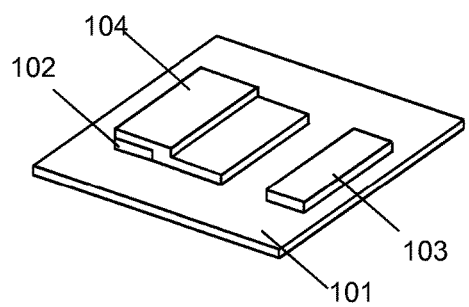

In this case, one of the proton-accepting electrode and proton-generating layers is then printed (as shown in FIG. 1c). In this case, the proton-generating electrode layer 104 is printed before the proton-accepting electrode layer. It will be appreciated that, in other embodiments, the proton-accepting electrode layer may be printed before the proton-generating electrode layer. In this case, the proton-generating electrode layer 104 comprises graphene based ink (in this case, comprising graphene oxide having one or more carboxyl, hydroxyl and/or epoxy groups). As shown in FIG. 1c, the proton-generating electrode layer 104 is connected to the first charge collector 102, by being printed over the first charge collector so that there is an area of overlap. There is no direct connection between the proton-generating electrode layer 104 and the second charge collector 103 to prevent short-circuit between the first and second charge collectors 102, 103. Also, because it is the junction between the proton-generating electrode layer and proton-accepting electrode layer that causes the voltage to be generated, both charge collectors should not be in electrical contact with one side of the junction.

When the graphene oxide (having one or more carboxyl, hydroxyl and/or epoxy groups) interacts with water, protonation occurs creating protons ($H^+$) and negatively charged functional groups (e.g. $COO^-$). In this way, water may be used to activate the proton-generating electrode layer.

Figure 1D:
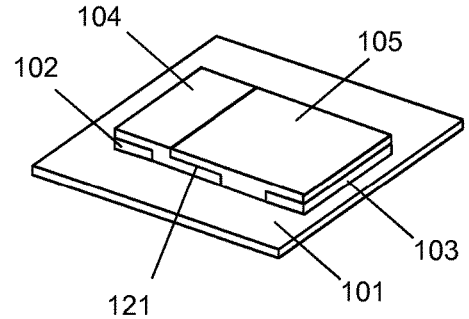

In this case, the other electrode layer (in this case, the proton-accepting electrode layer 105) is then printed as shown in FIG. 1d. As shown in FIG. 1d, the proton-accepting electrode layer 105 is connected to the second charge collector 103 (by being printed over the second charge collector 103 so that there is an area of overlap), but there is no direct connection between the proton-accepting electrode layer 105 and the first charge collector 102 (to prevent a short-circuit between the first and second charge collectors). In this case, the proton-accepting electrode layer 105 comprises reduced graphene based ink.

Depending on the state of the proton accepting and proton generating layers, a range of voltages may be produced. For example, reduced GO (rGO) produced using ascorbic acid can generate a voltage of 0.2 V, whereas reduced GO (rGO) produced using KOH (strong base) can give a higher voltage of 1.5 V. It will be appreciated that the voltage between charge collectors may also influenced by the internal resistance of the proton battery.

Because the proton-accepting electrode layer is printed partially over the proton-generating layer, there is an area of overlap between the proton-accepting electrode layer and the proton-generating layer. This area of overlap is the junction region 121 of the apparatus.

It will be appreciated that, in other example embodiments, an insulating layer may be printed over a first electrode layer in the region of the connected charge collector before the second electrode layer is printed. This insulating layer may help prevent the second electrode layer coming into proximity to the charge collector which is connected to the first electrode layer (and thereby help to prevent a short circuit).

Figure 1E:
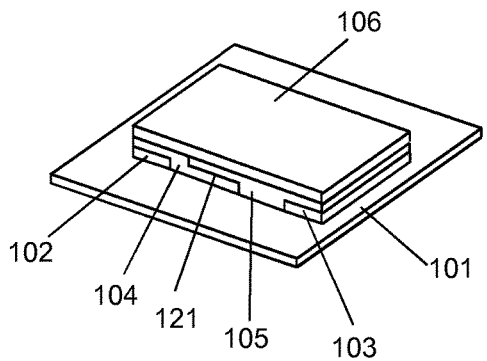

As shown in FIG. 1e, an electrolyte layer 106 is then provided on top. The electrolyte layer 106 may comprise for example, different types of room temperature ionic liquids, Nafion® or polyvinyl alcohol film. Polymer such as polyvinyl alcohol (PVA) and Nafion coated on top of the paper electronics may provide a source of trapped water that provides 'fuel' for the proton battery (by activating the proton-generating electrode layer) as well as a protective layer for the paper electronics. In this case, the electrolyte layer has two functions: first, it traps humidity to enable protonation; and secondly, its high ionic conductivity can lower the internal resistance of the proton battery. This may allow higher voltage to be achieved. It will be appreciated that in other embodiments, these functions may be provided by separate layers. Providing a source of water may help stabilise the voltage produced by the apparatus. It will be appreciated that other embodiments may rely on water absorbed from the environment (e.g. from the atmosphere) or on water stored in the substrate (e.g. in the porous structure of the paper substrate). Such embodiments may not have an electrolyte layer configured with the apparatus.

In this way, the 2D planar structure (2D because the structure is supported on one surface of the substrate) can enable the proton battery to be manufactured using print process such as, for example, roll-to-roll processing, ink-jet printing, and screen printing. Also because the electronically active components of the apparatus are supported on one surface of the substrate, more complex electronic circuits may be built up by arranging a number of connected apparatuses on a common substrate surface. For example, a battery with a number of cells may be produced on a surface of a single sheet of paper.

In this case, because a number of the components are printed using aqueous inks (e.g. the electrode layers and the charge carriers) a water-control layer may be used to restrict the area of the components. For example, if the reduced graphene oxide of the proton accepting layer was being printed in an area close to the first charge collector (e.g. within 0.5 mm), a water control layer may first be provided over the first charge control layer. This may help mitigate the chances of the aqueous reduced graphene oxide from seeping into the first charge collector and forming a short circuit.

Figure 1F:
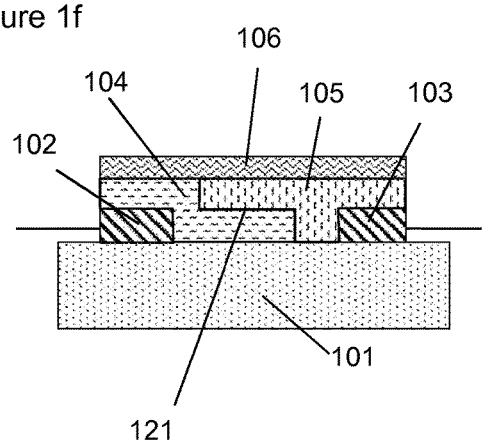
FIG. 1f shows a cross section of the battery cell.

FIG. 1f is a cross-section of the completed battery cell apparatus. It has been found that the bigger the overlapping junction area 121 between the proton-generating electrode layer 104 and the proton-accepting electrode layer 105, the bigger the current (or energy) that is available from the battery cell apparatus It will be appreciated that the voltage generated by the junction is related to the condition and material of the electrodes (e.g. how much water is present).

As noted above, in the presence of water, protonation occurs in the graphene oxide of the proton-generating layer. These protons may migrate to the proton-accepting layer leaving negatively charged functional groups (e.g. COO⁻) in the proton-generating layer. That is, the voltage produced is the result of a separation of charge between the proton accepting and proton generating layers. This charge separation may be the result of a pH gradient between the proton generating layer and the proton accepting layer; and/or differences in the electrochemical potential between the proton generating layer and the proton accepting layer.

Therefore, a voltage is created between the negative charge of the first charge collector and the positive charge of the second charge collector. This voltage can be extracted and used to power other electronic components. In this way, the apparatus operates as a battery cell. It will be appreciated that such a battery cell may be incorporated into a wide range of energy harvesting/storage devices.

It will be appreciated that the battery cell apparatus may comprise connectors for connecting the charge collectors to a circuit (which may be an external circuit or a circuit provided on the same substrate).

It will be appreciated that an array of interconnected apparatus embodiments as described above can be printed onto a single substrate. For example, by connecting a plurality of battery cell apparatuses in series, the voltage produced may be increased whereas connecting a plurality of battery cell in parallel would allow the energy stored in the composite device to be increased. Each of the constituent apparatuses may be considered to be a functional group. In this way, the connections allow the apparatuses to act in concert to provide a cumulative effect.

Figure 1G:
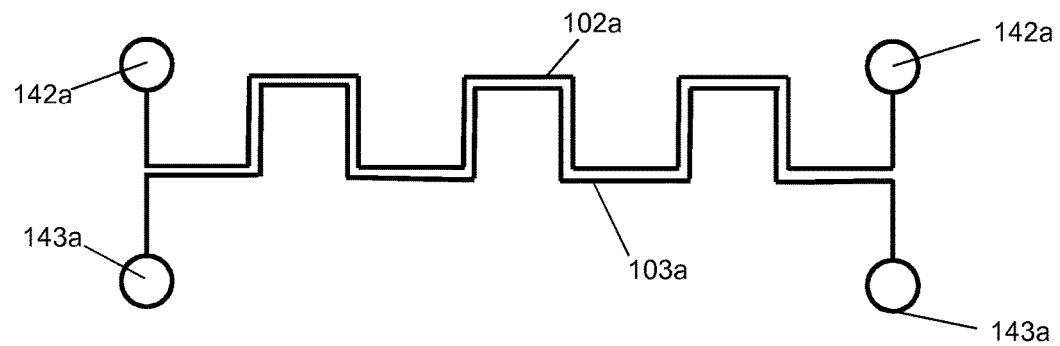
FIGS. 1g-i are plan views of charge carrier arrangements on a two-dimensional substrate.

FIG. 1g is a plan view of the first and second charge collectors 102a, 103a printed onto a two-dimensional substrate (such a piece of paper). Upon and between these charge collectors are printed the overlapping proton generating and proton accepting layers (these layers are not shown for clarity). The charge collectors are stepped to increase the area of the junction whilst ensuring that the junction region is not located too far away from the charge collectors. This helps increase the output voltage by minimising the effect of the relatively high resistance of the electrode layers. In this case, each of the charge carriers 102a, 103a is connected to two connectors 142a, 143a to allow the voltage to be provided to an external circuit.

Figure 1H:
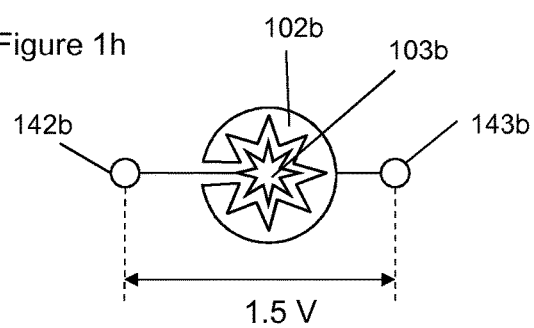

An alternative arrangement of charge carriers printed on a two-dimensional substrate is shown in FIG. 1h. In this case, the charge carrier 103b connected to the proton-generating layer (the proton-generating electrode layer, in this case, comprising graphene oxide) is towards the centre and is almost completely surrounded by the charge carrier 102b connected to the proton-accepting electrode layer (the proton-accepting electrode layer, in this case, comprising reduced graphene oxide). For clarity, the overlapping proton-accepting electrode layer and proton-generating electrode layer are not shown. The junction area in this case, is located between the rough (or jagged) interlocking edges of the charge carriers 102b, 103b. The rough interlocking edges of the charge carriers 102b, 103b are configured to increase the junction area whilst reducing the junction-charge carrier distance. In this case, each of the charge carriers 102b, 103b is connected to a connector 142b, 143b to allow the battery cell to be connected to an external circuit. In this case, the voltage generated between the external connectors of the battery cell is 1.5 volts.

Figure 1I:
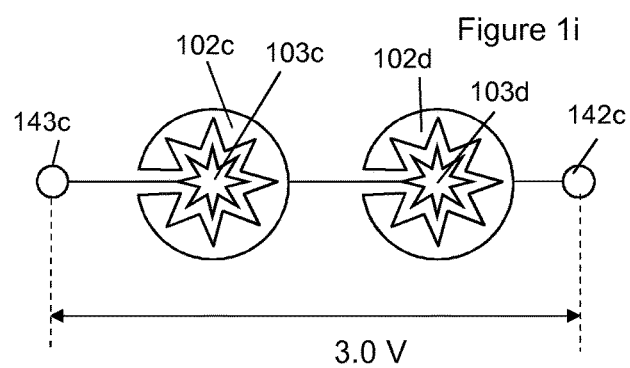

As shown in FIG. 1i, two battery cells such as are shown in FIG. 1g can be printed to interconnect such that the overall voltage generated by the two cells is 3.0 V. In this case the two cells are connected to connectors 142c, 143c to allow this voltage to be supplied to an external circuit. The increased voltage is produced by appropriately connecting the charge carriers of the component cells such that the cells are in series. In particular, the charge collector 103c connected to the proton-generating electrode layer of a first cell is connected to a first connector 143c. The charge collector 102c connected to the proton-accepting electrode layer of the first cell is connected to the charge collector 103d connected to the proton-generating layer of a second cell. The charge collector 102d connected to the proton-accepting electrode layer of the second cell is connected to a second connector 142c. It will be appreciated that may other configurations are possible.

In this case, the polymer electrolyte is configured to provide water to the graphene oxide layer to generate protons.

FIG. 2a-e shows the manufacture of an embodiment of a sensor apparatus, the apparatus comprising:
  an insulating substrate 201;
  at least two charge collectors 202, 203 spaced apart on the substrate surface;
  a proton-generating electrode layer 205 configured to generate proton charge carriers;
  a proton-accepting electrode layer 204 configured to accept the generated proton charge carriers,
  wherein each of the proton-generating electrode layer 205 and proton-accepting electrode layer are configured to be electrically connected to a different one of the respective charge collectors 202, 203, and to overlap in a junction region such that the charge carriers of the layers can be transferred between the proton-generating and proton-accepting electrode layers to thereby generate a voltage.

In this case, the sensor apparatus is configured to enable measurement of the relative humidity of the atmosphere.

Figure 2A:
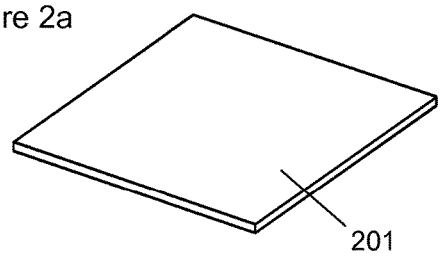
FIGS. 2a-e show a manufacturing process used to create a sensor.
Figure 2B:
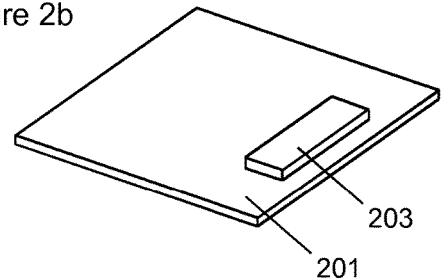

FIG. 2a shows the substrate 201, which in this case is paper (cellulose). Using a paper substrate allows the battery cell apparatus to be folded. It will be appreciated that in other example embodiments other substrate materials may be used, such as glass, silicon, silicon dioxide, polymers (e.g. polyethylene terephthalate, polyethylene naphthalate, polydimethylsiloxane or polyurethane) or other plastics.

To manufacture the sensor apparatus, a second charge collector 203 is printed onto a surface of the substrate (as shown in FIG. 2a). In this case, the second charge collector 203 comprises copper ink printed onto the surface of the substrate.

It will be appreciated that the charge collectors may be provided using inkjet, screen, stencil or flexographic printing; evaporation or sputtering. Suitable charge collector materials include metals such as gold, silver and copper; and printed metals such as silver nanoparticles.

Figure 2C:
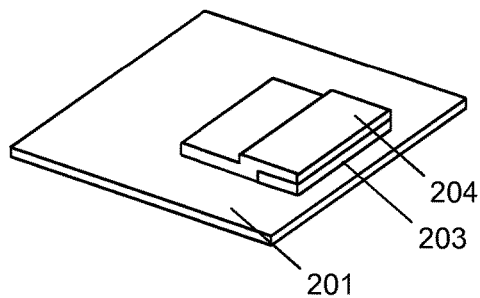

Then one of the electrodes are printed (as shown in FIG. 2c). In this case, the proton-accepting electrode layer 204 is printed before the proton-generating electrode layer. It will be appreciated that, in other embodiments, the proton-accepting electrode layer may be printed after the proton-generating electrode layer. In this case, the proton-accepting electrode 204 comprises graphene based ink (in this case, comprising reduced graphene oxide). As shown in FIG. 2c, the proton-accepting electrode layer 204 is connected to the second charge collector 203.

Graphene oxide may comprise a plurality of fully or partially oxidised graphene flakes with various functional groups attached thereto. Furthermore, the size and number of the oxidised graphene layers may vary. Graphene oxide solution (concentration: 1 g/L; composition: carbon (79%), oxygen (20%); flake size: 0.5-0.7 µm; and thickness: 1 atomic layer (at least 60%)) can be obtained from Graphene Square, Inc and deposited using spray coating, drop casting, spin coating or inkjet printing.

Figure 2D:
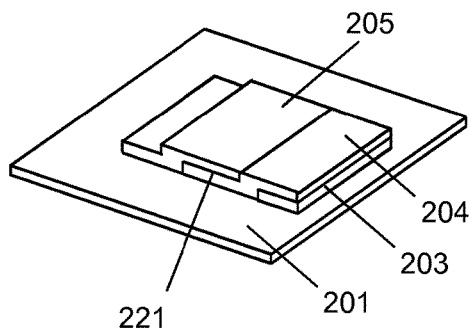

Then, the other electrode layer (in this case the proton-generating electrode layer 205) is printed as shown in FIG. 2d. There is no direct connection between the proton-generating electrode layer 205 and the second charge collector 203. In this case, the proton-generating electrode comprises graphene based ink.

Because the proton-accepting electrode layer is printed partially over the proton-generating layer, there is an area of overlap between the proton-accepting electrode layer and the proton-generating layer. This area of overlap is the junction region.

Figure 2E:
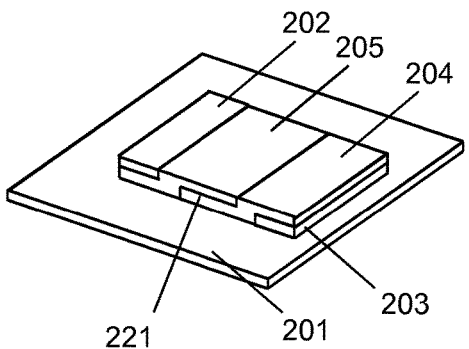

Finally (as shown in FIG. 2e), a first charge collecting layer 202 is printed to collect charge from the proton-generating layer 205. In this way, the 2D planar structure can enable the sensor to be manufactured using print process such as, for example, roll-to-roll processing, ink-jet printing, and screen printing. Although the first charge collecting layer 202 is not in direct contact with the substrate, it is still positioned on the substrate as it is being supported by the substrate. The first charge collecting layer 202 is spaced apart from the second charge collector 203 on the substrate surface to prevent a short-circuit between the charge collectors.

Figure 2F:
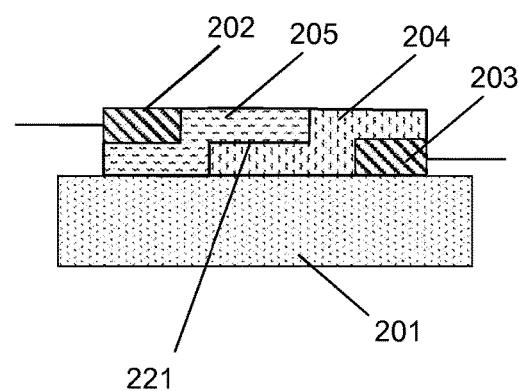
FIG. 2f shows a cross section of the sensor.

FIG. 2f is a cross-section of the completed sensor apparatus. It has been found that the bigger the overlap area of the junction region 221 between the proton-generating electrode layer and the proton-accepting electrode layer, the bigger the current that is available. That is, the energy which the battery cell can store is related to (e.g. proportional to) the area of the overlap. The voltage generated by the junction is related to the condition and material of the electrodes rather than the area of overlap.

As noted above, in the presence of water, protonation occurs in the graphene oxide of the proton-generating layer. These protons may migrate to the proton-accepting layer leaving negatively charged functional groups (e.g. COO⁻) in the proton-generating layer. That is, the voltage produced is the result of a separation of charge between the proton accepting and proton generating layers. This charge separation may be the result of a pH gradient between the proton generating layer and the proton accepting layer; and/or differences in the electrochemical potential between the proton generating layer and the proton accepting layer. The pH gradient may be a result of the proton-generating layer being acidic and the proton-accepting layer being alkali.

Therefore, a voltage is created between the negative charge of the first charge collector 202 and the positive charge of the second charge collector 203 in response to fluid being present in the proton-generating layer. In this way, the voltage generated may be used as a measure of the quantity of fluid present in the atmosphere surrounding the sensor. That is, the sensor may be used to measure, for example, the relative humidity of the atmosphere. The term "relative vapour pressure" may be taken to mean the ratio between the partial vapour pressure of a fluid and its saturation vapour pressure at a given temperature. It may be advantageous to have the proton-generating layer 203 exposed to the atmosphere (as is the case in the present embodiment) to provide a more accurate and/or responsive determination of the humidity in the atmosphere.

It will be appreciated that the apparatus may comprise connectors for connecting the charge collectors to a circuit (which may be an external circuit or a circuit provided on the same substrate). The external circuit may comprise a processor and a memory comprising computer program code. In this case, such a processor may be configured, with the memory and computer program code, to convert the value of the voltage produced into a humidity measurement.

It will be appreciated that if water was provided to the proton-generating layer 205 the resulting voltage may be used to power other electronics. In this way, the sensor structure may be used as a battery cell apparatus.

Since graphene inks can be coated on most substrates, embodiments may include wearable electronics. For example, electrodes may be provided onto a cloth or rubber substrate to form part of, for example, gloves or other clothing.

Because embodiments may be printed cheaply, embodiments may be used in distributed sensing systems and distributed sensor stickers and/or tags. For example, printed posters may incorporate embodiments, for example, to generate power for active display screens.

Figure 3:
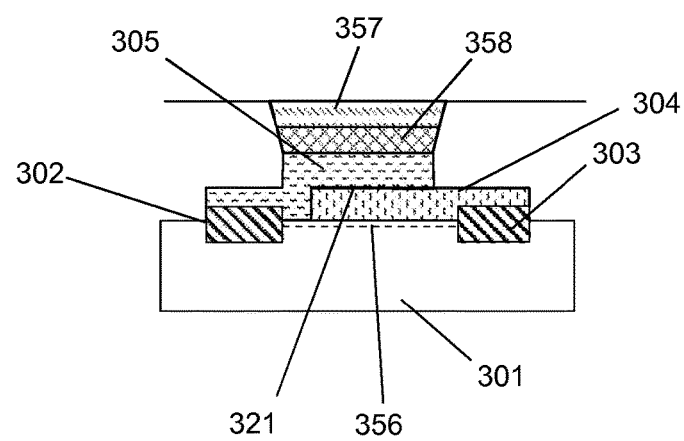
FIG. 3 shows a cross-section of a chemical FET sensor.

FIG. 3 illustrates a chemical FET embodiment incorporating a proton junction. The embodiment of FIG. 3 is similar to that of FIG. 2f. However, rather than measuring the voltage generated by the junction, the voltage generated is used to control the flow of electrons through a channel 356.

The chemical field-effect transistor embodiment of FIG. 3 comprises:
an insulating substrate 301, which in this case is paper;
at least two charge collectors 302, 303 spaced apart on the substrate surface;
a proton-generating electrode layer 305 configured to generate proton charge carriers;
a proton-accepting electrode layer 304 configured to accept the generated proton charge carriers,
wherein each of the proton-generating electrode layer and proton-accepting electrode layer are configured to be electrically connected to a different one of the respective charge collectors, and to overlap in a junction region such that the charge carriers of the layers can be transferred between the proton-generating and proton-accepting electrode layers to thereby generate a voltage.

In this case, the sensor apparatus further comprises a membrane 357 and a hydrogel 358. When the humidity of the atmosphere (or pH) increases, more protons are generated by the graphene oxide proton-generating electrode layer. This changes the voltage between the source charge carrier and the drain charge carrier. That is, change in the junction region (caused by different humidity/pH) causes the gate voltage to change. Other chemical FET embodiments may be configured to measure the pH a solution.

Figure 4:
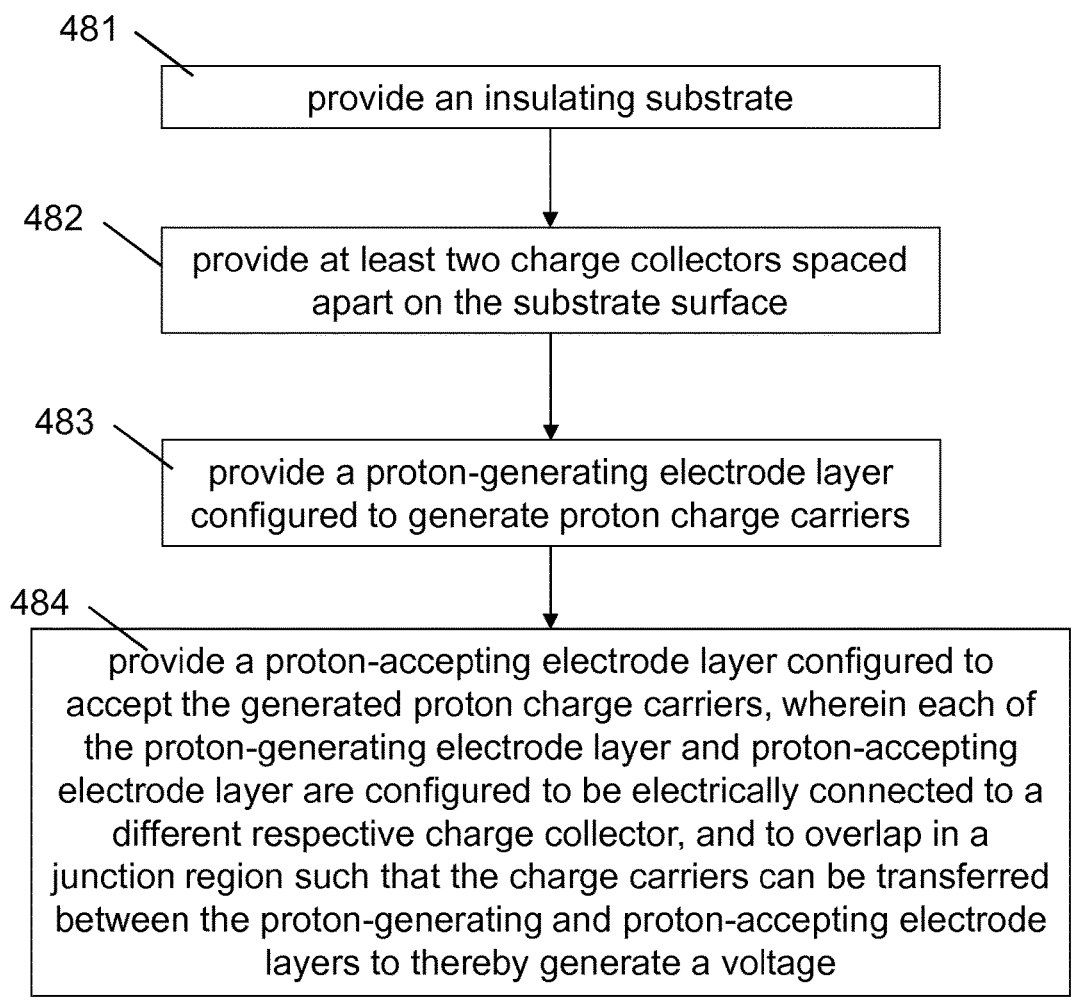
FIG. 4 shows the manufacturing process.

FIG. 4 illustrates the process flow according to an example embodiment of the present disclosure. The process comprises providing 481 an insulating substrate; providing 382 at least two charge collectors spaced apart on the substrate surface; providing 483 a proton-generating electrode layer configured to generate proton charge carriers; providing 484 a proton-accepting electrode layer configured to accept the generated proton charge carriers, wherein each of the proton-generating electrode layer and proton-accepting electrode layer are configured to be electrically connected to a different one of the respective charge collectors, and to overlap in a junction region such that the charge carriers of the layers can be transferred between the proton-generating and proton-accepting electrode layers to thereby generate a voltage. It will be appreciated that, in other embodiments, the provision of each of the charge collectors and each of the electrode layers may be carried out in any order.

Figure 5:
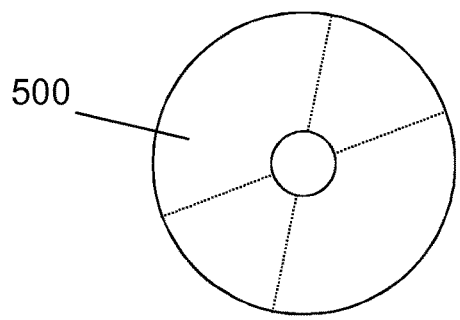
FIG. 5 shows a computer program product embodiment.

FIG. 5 illustrates schematically a computer/processor readable medium 500 providing a computer program according to one embodiment. In this example, the computer/processor readable medium 500 is a disc such as a digital versatile disc (DVD) or a compact disc (CD). In other embodiments, the computer/processor readable medium 500 may be any medium that has been programmed in such a way as to carry out an inventive function. The computer/processor readable medium 500 may be a removable memory device such as a memory stick or memory card (SD, mini SD, micro SD or nano SD).

The computer program may comprise computer code configured to perform, control or enable one or more of the method steps 481-484 of FIG. 4. For sensor embodiments, the computer program may be configured to measure/calculate the voltage produced, and determine the relative vapour pressure of the fluid in the environment based on the measured/calculated voltage. Additionally or alternatively, the computer program may be configured to control the above-mentioned fabrication processes.

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus, the apparatus comprising:
   an insulating substrate;
   at least two charge collectors spaced apart on the substrate surface;
   a proton-generating electrode layer configured to generate proton charge carriers;
   a proton-accepting electrode layer configured to accept the generated proton charge carriers,
   wherein each of the proton-generating electrode layer and proton-accepting electrode layer are configured to be electrically connected to a different one of the respective charge collectors, and to overlap in a junction region such that the charge carriers of the layers can be transferred between the proton-generating and proton-accepting electrode layers to thereby generate a voltage.

2. The apparatus of claim 1, wherein the proton-generating electrode layer comprises graphene oxide.

3. The apparatus of claim 1, wherein the proton-accepting electrode layer comprises reduced graphene oxide.

4. The apparatus of claim 1, wherein at least one of the electrode layers comprise one or more of a plurality of fully or partially oxidised graphene flakes.

5. The apparatus of claim 1, wherein protons charge carriers are generated by charge-releasing functional groups, the charge-releasing functional groups comprising one or more of a carboxyl, hydroxyl and epoxy group.

6. The apparatus of claim 1, wherein the substrate is at least one of: a flexible substrate; a resilient substrate; and a foldable substrate.

7. The apparatus of claim 1, wherein the substrate comprises at least one of: a polymer sheet, and glass.

8. The apparatus of claim 1, wherein the substrate comprises paper.

9. The apparatus of claim 1, wherein at least one of the charge collectors comprise silver or copper.

10. The apparatus of claim 1, wherein at least one of the charge collectors and the electrode layers are printed onto the substrate.

11. The apparatus of claim 1, wherein at least one of the charge collectors and the electrodes are formed from ink.

12. The apparatus of claim 1, wherein the apparatus comprises an electrolyte layer.

13. The apparatus of claim 12, wherein the electrolyte layer comprises Nafion® or polyvinyl alcohol film.

14. The apparatus of claim 1, wherein the apparatus comprises a protective layer covering at least the proton-generating layer, the protective layer comprising a fluid-impermeable material.

15. The apparatus of claim 1, wherein the apparatus comprises one or more of a battery cell, a FET and a sensor.

16. The apparatus of claim 1, wherein the proton-generating layer is configured to generate proton in response to a fluid being present, such that the voltage produced may be used as an indicator of the amount of fluid present.

17. A device comprising an array of connected apparatuses as recited in claim 1, wherein the connected apparatuses are arranged on a common substrate, the connections being configured to allow the apparatuses to act in concert to provide a cumulative effect.

18. A method for manufacturing an apparatus, the method comprising:
   providing an insulating substrate;
   providing at least two charge collectors spaced apart on the substrate surface;
   providing a proton-generating electrode layer configured to generate proton charge carriers;
   providing a proton-accepting electrode layer configured to accept the generated proton charge carriers,
   wherein each of the proton-generating electrode layer and proton-accepting electrode layer are configured to be electrically connected to a different one of the respective charge collectors, and to overlap in a junction region such that the charge carriers of the layers can be transferred between the proton-generating and proton-accepting electrode layers to thereby generate a voltage.

19. The method of claim 18, wherein at least one of the charge collectors and the electrodes are provided on the substrate by a printing process.

* * * * *